(12) United States Patent
Kelley et al.

(10) Patent No.: US 10,816,530 B2
(45) Date of Patent: Oct. 27, 2020

(54) SUBSTRATE CONTAINING LATENT VAPORIZATION REAGENTS

(71) Applicant: Massachusetts Institute of Technology, Cambridge, MA (US)

(72) Inventors: Jude Aaron Kelley, Bolton, MA (US); Richard Paul Kingsborough, Groton, MA (US); Roderick Russell Kunz, Acton, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 71 days.

(21) Appl. No.: 15/687,010

(22) Filed: Aug. 25, 2017

(65) Prior Publication Data
US 2018/0059086 A1    Mar. 1, 2018

Related U.S. Application Data

(63) Continuation-in-part of application No. 14/679,891, filed on Apr. 6, 2015, and a continuation-in-part of (Continued)

(51) Int. Cl.
*G01N 33/22* (2006.01)
*G01N 27/62* (2006.01)
(Continued)

(52) U.S. Cl.
CPC .......... *G01N 33/227* (2013.01); *G01N 1/44* (2013.01); *G01N 27/622* (2013.01);
(Continued)

(58) Field of Classification Search
CPC ........ G01N 1/44; G01N 27/622; G01N 33/22; G01N 33/227; H01J 49/0031;
(Continued)

(56) References Cited

U.S. PATENT DOCUMENTS 4,201,839 A    5/1980  Johnson et al.
4,242,097 A    12/1980 Rich, Jr. et al.
(Continued)

FOREIGN PATENT DOCUMENTS

EP    1145005 A3    10/2001
EP    1844189 A4    10/2007
(Continued)

OTHER PUBLICATIONS

Kelley et al. Rapid Communications in Mass Spectrometry, vol. 30, pp. 191-198, first published Dec. 13, 2015.*
(Continued)

*Primary Examiner* — Maureen Wallenhorst
(74) *Attorney, Agent, or Firm* — Nelson Mullins Riley & Scarborough LLP; Thomas J. Engellenner; Reza Mollaaghababa (57) ABSTRACT

Methods and reagents are disclosed for improved detection of inorganic oxidizers, such as but not limited to chlorates, perchlorates, permanganates, dichromates, and osmium tetraoxides. In one aspect of the invention, latent acid-generating reagents are employed that are chemically stable at room temperature but undergo an acidic transformation when exposed to an elevated temperature or radiation. The latent reagent can be activated by heat or radiation (e.g., UV radiation). The resulting acidic reagent can then transfer a proton to the anion (i.e., chlorate, perchlorate, etc.) of the target analyte, forming an acid (i.e., chloric acid, perchloric acid) that is more easily vaporized and, hence, more easily detected. In another aspect of the invention, heat-sensitive inorganic salts and/or photosensitive onium salts are disclosed as reagents to carry out this method. In various embodiments, these reagents can be embedded in a swipe or other substrate, infused onto the swipe or sample via nebu-
(Continued)

lizer, or otherwise deployed in a desorption chamber of an ion mobility spectrometer or similar detector.

19 Claims, 6 Drawing Sheets

Related U.S. Application Data application No. 13/948,423, filed on Jul. 23, 2013, now Pat. No. 9,588,095.

(60) Provisional application No. 62/379,774, filed on Aug. 26, 2016.

(51) Int. Cl.
  *G01N 1/44* (2006.01)
  *H01J 49/00* (2006.01)

(52) U.S. Cl.
  CPC ......... *H01J 49/0031* (2013.01); *Y10T 436/19* (2015.01); *Y10T 436/24* (2015.01)

(58) Field of Classification Search
  CPC ... Y10T 436/19; Y10T 436/24; Y10T 436/16; Y10T 436/163333; Y10T 436/17; Y10T 436/173076; Y10T 436/18; Y10T 436/25; Y10T 436/25875
  USPC ... 436/75, 79, 110, 119, 103, 104, 147, 124, 436/164, 166, 169, 173, 174, 181
  See application file for complete search history.

(56) References Cited

U.S. PATENT DOCUMENTS

| | | | |
|---|---|---|---|
| 4,387,164 A | 6/1983 | Hevey et al. | |
| 4,562,148 A | 12/1985 | Sommer | |
| 4,752,448 A | 6/1988 | Wells et al. | |
| 5,157,260 A | 10/1992 | Mylchreest et al. | |
| 5,296,380 A | 3/1994 | Margalit | |
| 5,352,893 A | 10/1994 | Freedman | |
| 5,756,994 A | 5/1998 | Bajic | |
| 5,988,002 A | 11/1999 | Danylewych-May et al. | |
| 6,287,780 B1 | 9/2001 | Schmidt et al. | |
| 6,627,444 B1 | 9/2003 | Goledzinowski et al. | |
| 7,078,237 B1 | 7/2006 | Mowry et al. | |
| 7,439,496 B2 | 9/2008 | Stott et al. | |
| 7,534,844 B2 | 5/2009 | Kwak | |
| 7,598,488 B2 | 10/2009 | Park | |
| 7,638,266 B2 | 12/2009 | Angelopoulus et al. | |
| 8,119,984 B2 | 2/2012 | Shabanowitz et al. | |
| 8,217,340 B2 | 7/2012 | Yoshimura et al. | |
| 8,304,251 B2 | 11/2012 | Haas et al. | |
| 8,513,596 B2 | 8/2013 | Kang et al. | |
| 9,588,095 B2 * | 3/2017 | Gregory ............... | G01N 33/227 |
| 9,689,857 B1 * | 6/2017 | Vilkov ................. | G01N 33/227 |
| 10,345,281 B2 * | 7/2019 | Kelley ................. | G01N 33/227 |
| 2004/0157344 A1 | 8/2004 | Wang et al. | |
| 2005/0288616 A1 | 12/2005 | Bozenbury, Jr. et al. | |
| 2006/0192098 A1 | 8/2006 | Danylewych-May | |
| 2007/0069120 A1 | 3/2007 | Shvartsburg et al. | |
| 2008/0101995 A1 | 5/2008 | Gabowitcz et al. | |
| 2008/0128608 A1 | 6/2008 | Northen et al. | |
| 2008/0245963 A1 | 10/2008 | Land et al. | |
| 2009/0032701 A1 | 2/2009 | Rodier | |
| 2009/0039243 A1 | 2/2009 | Wynn et al. | |
| 2009/0078862 A1 | 3/2009 | Rodier et al. | |
| 2009/0269855 A1 | 10/2009 | Wang et al. | |
| 2010/0047849 A1 | 2/2010 | Caulfield et al. | |
| 2010/0291704 A1 | 11/2010 | Cody | |
| 2011/0081723 A1 | 4/2011 | Miller et al. | |
| 2011/0101216 A1 | 5/2011 | Musselman | |
| 2012/0119079 A1 | 5/2012 | Ouyang et al. | |
| 2012/0149006 A1 | 6/2012 | Padilla De Jesus et al. | |
| 2012/0181421 A1 | 7/2012 | Satoh et al. | |
| 2012/0187287 A1 * | 7/2012 | Nyman ............... | H01J 49/0418 |
| | | | 250/282 |
| 2014/0030816 A1 | 1/2014 | Gregory et al. | |
| 2014/0065550 A1 | 3/2014 | Kramer et al. | |
| 2016/0161379 A1 * | 6/2016 | Hendrikse ............ | G01N 1/02 |
| | | | 436/124 |
| 2017/0284977 A1 * | 10/2017 | Rogers ................. | G01N 30/12 |
| 2019/0011421 A1 * | 1/2019 | Rogers ................ | G01N 33/227 |

FOREIGN PATENT DOCUMENTS

| | | | |
|---|---|---|---|
| EP | 3012626 | * | 4/2016 |
| WO | 9905319 A2 | | 2/1999 |
| WO | 0075372 A1 | | 12/2000 |
| WO | 2007066240 A2 | | 6/2007 |
| WO | 2009152276 A2 | | 12/2009 |
| WO | 2011144743 A1 | | 11/2011 |

OTHER PUBLICATIONS

Peng et al. Scientific Reports, vol. 4:6631, pp. 1-5, Oct. 16, 2014.*
"18-Crown-6" accessed by examiner at [http://www.chemicalland21.com/lifescience/phar/18-crown-6.htm] on Apr. 1, 2014.
3-Pyridinecarboxamide (nicotinamide) (UNEP Publications Oct. 2002) accessed by examiner at [http://www.inchem.org/documents/sids/sids/98920.pdf].
Badu-Tawiah et al.,Reactions of microsolvated organic compounds at ambient surfaces: Droplet velocity, charge state, and solvent effects. Journal of the American Society for Mass Spectrometry 2012, 23 (6), 1077-1084.
Benassi et al., Redox transformations in desorption electrospray ionization. International Journal of Mass Spectrometry 280 (2009) 235-240.
Brodbelt et al., New frontiers in host-guest chemistry—the gas phase. Pure and applied Chemistry 1993, 65 (3) 409-414.
Chu et al., Macrocyclic chemistry in the gas phase-intrinsic caton affinities and complexion rates for alkali-metal cation complexes of crown-ethers. Journal of the American Chemical Society 1993, 115 (13), 5736-5744.
de Perre et al.,Rapid and specific detection of Urea nitrate and ammonium nitrate by electrospray ionization time-of-flight mass spectrometry using infusion with crown ethers.Rapid Communications in Mass Spectrometry 2012, 26(2), 154-162.
Dietrich et al., Stability, molecular-dynamics in solution, and x-ray structure of the ammonium cryptate NH4+ subset of 2.2.2.PF6. Journal of Physical Chemistry 1987, 91 (27), 6600-6606.
Eiceman et al., Enhanced selectively in ion mobility spectrometry analysis of complex mixtures by alternate reagent gas chemistry. Analytica Chimica Acta 1995, 306 (1), 21-33.
Evans et al., A rapid and efficient mass spectrometric method for the analysis of explosives. Rapid Communications in Mass Spectrometry 2002, 16 (19), 1883-1891.
Ewing et al., A critical review of ion mobility spectrometry for the detection of explosives and explosive related compunds. Talanta 2001, 54 (3), 515-529.
Fieser., Fiesers' Reagents for Organic Synthesis, vol. 27, JohnWiley & Sons, 2011 Table of Contents.
Flanigan et al., Determination of Inorganic Improvised Explosive Device Signatures Using Laser Electrospray Mass Spectrometry Detection with Offline Classification. Analytical Chemistry 2011, 83 (18) 7115-7122.
Graf et al., Molecular recognition-selectiveammonium cryptates of synthetic receptor molecules possessing a tetrahedral recognition site. Journal of the American Society 1982, 104 (6), 1672-1678.
IARC Monographs vol. 73 "HEXACHLOROETHANE" was accessed by the examiner from [http://monographs.iarcs.fr/ENG/Monographs/vol73/mono73-15.pdf] on Dec. 22, 2014.
International Preliminary Report on Patentability received in PCT/US2013/051676 dated Feb. 5, 2015; 8 pages.
International Search Report and Written Opinion received in PCT/US2013/051676 dated May 27, 2014; 11 pages.
International Search Report and Written Opinion received in PCT/US2015/24560 dated Jun. 29, 2015; 13 pages.

(56) References Cited

OTHER PUBLICATIONS

Kozole et al., Characterizing the gas phase ion chemistry of an ion trap mobility spectrometry based explosive trace detector using a tandem massspectrometer. Talanta 2012, 99, 799-810.

Lawrence et al., Detection of ethylene glycol dinitrate vapors by ion mobility spectrometry using chloride reagent ions. Analytical Chemistry 1988, 60 (2), 104-109.

Li et al., Reversed-phase liquid chromatography/electrospray ionization/mass spectrometry with isotope dilution for the analysis of nitrate and nitrite in water. Journal of Chromatography A. Jan. 21, 2011; 1218 (3): 476-483.

Maleknia et al., Cavity-size-dependent dissociation of crown-ether ammonium ion complexes in the gas-phase. Journal of the American Chemical Society 1993, 115(7), 2837-2843.

McDougall et al. The identification of traces of explosives by field spot tests in Ministry of Defense Explosives Research and Development Establishment, Technical Report No. 122, Mar. 1973.

More et al., Intrinsic affinities of alkali cations for 15-crown-5 and 18 crown-6: Bond dissociation energies of gas-phase M+crown ether complexes. Journal of the American Chemical Society 1999, 121 (2) 417-423.

Morkoc., "Handbook of Nitride Semiconductors and Devices, Materials Properties, Physics and Growth" Jul. 30, 2009.

Office Action received in related U.S. Appl. No. 13/948,423 dated Aug. 10, 2016; 18 pages.

Park et al., Surprisingly stable ammonium ion complex of a non-cyclic crown-type polyether: Solid and solution studies. New Journal of Chemistry 2010, 34(4), 603-606.

Sakayanagi et al., Identification of inorganic anions by gas chromatography/mass spectrometry. Forensic Sci Int. Mar. 10, 2006;157(2-3):134-143.

Sassine et al., An electrospray ionization tandem mass spectrometric study of p-tert-butylcalix [6] arene complexation with ammonium hydroxide, and ammonium and sodium ions. Rapid communications in Mass Spectrometry 2008, 22(3), 385-393.

Schenderlein et al.,Preparation and characterization of light-switchable polymer networks attached to solid substrates. Langmuir. Apr. 9, 2013;29(14):4525-34.

"Schmitt-Kopplin P et al., Capillary electrophoresis-electrosprayionization-mass spectrometry for the characterization of natural organic matter:an evaluation with free flow electrophoresis-off-line flow injection electrosprayionization-mass spectrometry. Electrophoresis. Sep. 2003;24(17):3057-66."

Smith ., March's Advanced Organic Chemistry: Reactions, Mechanisms and Structure, 7th Edition, Wiley & Sons, 2013. Table of contents.

Spath et al., Molecular recognition of organic ammonium ions in solution using systhetic receptors. Beilstein Journal of Organic Chemistry 2010, 6.

Sundberg et al., Advanced Organic Chemistry, Part13: Reactions and Synthesis, 5th Edition, Springer, 2007. Table of contents.

Taylor et al., A mass spectrometric study of glucose, sucrose, and fructose using and inductively coupled plasma and electrospray ionization. International Journal of Mass Spectrometry 2005, 243 (1), 71-84.

Tsai et al., Analysis of ammonium nitrate/urea nitrate with crown ether and sugar as modifiers American Society for Mass Spectrometry, Denver 2011.

Urbansky et al., Quantitation of perchlorate ion by electrospray ionization mass spectrometry (ESI-MS) using stable association complexes with organic cations and bases to enhance selectivity, Journal of Analytical Atomic Spectrometry 1999, 14, 1861-1866.

Yanes et al., "Nanostructure Initiator Mass Spectrometry: Tissue Imaging and Direct Biofluid Analysis" Anal. Chem. 2009, 81, 2969-2975.

Yongtao et al., "Reversed-phased liquid chromatography/electrospray ionization/mass spectrometry with isotope dilution for the analysis of nitrate and nitrate in water" Journal of Chromatography A, 1218 (2011) 476-483.

International Preliminary Report on Patentability for PCT/US2013/051676, dated Jan. 27, 2015: 7 pages.

International Search Report and Written Opinion for PCT/US2013/051671, dated Apr. 4, 2014, 9 pages.

Oscar Yanes, Hin-Koon Woo, Trent R. Northen, Stacey R. Oppenheimer, Leah Shriver, Jon Apon, Mayra N. Estrada, Michael J. Potchoiba, Rick Steenwyk, Marianne Manchester, and Gary Siuzdak "Nanostructure Initiator Mass Spectrometry: Tissue Imaging and Direct Biofluid Analysis" Anal. Chem. 2009, 81, 2969-2975.

Hadis Morkoc, Chapter 3—Growth and Growth Methods for Nitride Semiconductors, "Handbook of Nitride Semiconductors and Devices, Materials Properties, Physics and Growth" Jul. 30, 2009, p. Nos. 323-816.

International Search Report and Written Opinion for PCT/US2013/051676, dated May 27, 2014 10 pages.

International Preliminary Report on Patentability for PCT/US2013/051671, dated Jan. 27, 2015: 8 pages.

Office Action dated Jan. 31, 2018, in related U.S. Appl. No. 14/679,891, pp. (17).

\* cited by examiner

Step 1.  Contact sample with latent reagent

Step 2.  Activate latent reagent

Step 3.  React activated reagent with analyte

Step 4.  Detect analyte analog by mass spectrometry

SUBSTRATE CONTAINING LATENT VAPORIZATION REAGENTS

REFERENCE TO RELATED APPLICATIONS

The present application claims priority to U.S. Provisional Patent Application No. 62/379,774 entitled "Substrate Containing Latent Vaporization Reagents," filed on Aug. 26, 2016, which is herein incorporated by reference in its entirety. This application is also a continuation-in-part of U.S. patent application Ser. No. 14/679,891 entitled "Reagents For Enhanced Detection of Low Volatility Analytes" filed Apr. 6, 2015, now U.S. Pat. No. 10,345,281 and also a continuation-in-part of U.S. patent application Ser. No. 13/948,423 entitled "Reagents For Oxidizer-Based Chemical Detection" filed Jul. 23, 2013, now U.S. Pat. No. 9,588,095, both of which are likewise herein incorporated by reference in its entirety.

GOVERNMENT RIGHTS

This invention was made with U.S. government support under Interagency Agreements HSHQDC-09-X-00439 and HSHQPM-12-X-00057 by the U.S. Department of Homeland Security, Science and Technology Directorate, and performed by MIT Lincoln Laboratory under Air Force Contract No. FA8721-05-C-0002. The U.S. government has certain rights in the invention.

BACKGROUND OF INVENTION

The technical field of this invention is spectrometry, e.g., ion mobility spectrometry and the like, and in particular methods and reagents that can enhance the ionization of low volatility analytes.

The threats posed by concealed explosives and the intentional release of toxic chemicals continue to drive improvements in ways to detect these threats as a means to protect the public. One technique used to aid in this mission involves identification of the threat molecule by first ionizing it, and then detecting whether the threat molecule (analyte) is present. Ion mobility spectrometry (IMS), differential mobility spectrometry (DMS), field asymmetric ion mobility spectrometry (FAIMS), and mass spectrometry (MS) are all methods used to identify molecules that first require ionization. Given the importance of these techniques to public safety, considerable effort has been devoted to develop the best means to collect the sample from the environment, present the sample to the instrument, and to also ionize it efficiently and, if possible, selectively in order to provide the greatest detection capability. In almost all instances, the ionization is achieved at ambient-pressure using a technique called ambient-pressure ionization (API) (also sometimes called atmospheric-pressure chemical ionization). Because the ionization occurs in the gas phase through ion-molecule collisions, it is usually essential that the analyte is first vaporized to be present in the gas phase.

However, many of the explosive and chemical threats have low vapor pressure and exist as traces of solid particulates or thin films on surfaces, and thus the most common way to collect the sample requires a swipe or swab substrate which provides a physical mechanism to both collect and pre-concentrate the sample off the contaminated surface for subsequent presentation to the ionization space of the detection instrument. The substrate medium, or "swipe", containing the collected sample can be used to present the sample to the ionization instrument in one of two ways. In the first method, the swipe can be extracted using a solvent to selectivity dissolve the collected analyte into a solvent liquid, which is then presented to the ionization space of the instrument via a process called electrospray ionization. (See U.S. Pat. Nos. 8,513,596; 5,157,260; and 5,756,994, for examples of this approach). This requires extraction, dissolution, and injection steps and, although effective, is not practical in field settings. The alternative, and currently preferred method, is to heat the swipe to desorb the target chemical into the vapor phase for subsequent ionization and detection.

In a typical API system, a swipe or swab substrate is positioned in a thermal desorber located on the inlet side of the detection system. Thermal heating of the solid analyte particles on the swipe induces a solid-to-vapor phase transition and releases the analyte molecules as a vapor, usually guided into the sensor inlet by a carrier gas, and ionization occurs in the vapor phase. Properties of commercially available swipe media have been optimized over the years for increased efficiency of particle collection from surfaces (mechanical or electrostatic), efficient transfer and release of analyte into the chemical sensor, thermal stability, and low chemical background of the substrate. Prior art exists in the patent literature on different embodiments of sampling swipes (e.g., US2006-0192098; EP1844189 and WO2007-066240). See also, commonly-owned U.S. Pat. No. 9,891,193 entitled "Reagent Impregnated Swipe for Thermal Desorption Release and Chemical Detection with Ambient Ionization Techniques," which discloses reagents that are chemically embedded in the swipe material for interaction with the analyte (also incorporated herein by reference).

Sample collection via swipes is currently used in fielded IMS systems that detect explosives, where detection relies on efficient collection and presentation of low-vapor-pressure analytes such as 2,4,6-trinitrotoluene (TNT), 1,3,5-trinitro-1,3,5-triazacyclohexane (RDX) and pentaerythritol tetranitrate (PETN) into the instrument, and desorption temperatures in the range of 150 to 220° C.

Unfortunately, many homemade explosives (HMEs) pose particular challenges for API-based trace detection systems due to their wide range of properties, most notably their vapor pressures and resulting difficulties in achieving acceptable vapor pressures at the usual desorption temperatures of 150 to 220° C. For example, materials such as the sodium and potassium salts of chlorate and perchlorate do not have appreciable vapor pressures to allow for sensitive detection at temperatures less than 250° C. This also applies to salts containing nitrate, permanganate, and dichromate. Reagents that can convert these compounds to more volatile inorganic acids (e.g., chloric acid) can thus provide one means to improve performance of such API-based detection systems.

SUMMARY OF THE INVENTION

Methods and reagents are disclosed for improved detection of inorganic oxidizers, such as but not limited to chlorates, perchlorates, permanganates, dichromates, and osmium tetraoxides. In one aspect of the invention, latent acid-generating reagents are employed that are chemically stable at room temperature but undergo an acidic transformation when exposed to an elevated temperature or radiation. The latent reagent can be activated by heat or radiation (e.g., UV radiation). The resulting acidic reagent can then transfer a proton to the anion (i.e., chlorate, perchlorate, etc.) of the target analyte, forming an acid (i.e., chloric acid, perchloric acid) that is more easily vaporized and, hence, more easily detected. In another aspect of the invention, heat-sensitive inorganic salts and/or photosensitive onium salts are disclosed as reagents to carry out this method. In various embodiments, these reagents can be embedded in a swipe or other substrate, infused onto the swipe or sample via nebulizer, or otherwise deployed in a desorption chamber of an ion mobility spectrometer or similar detector.

The volatilization reagents described herein offer distinct advantages over current approaches and offer improved detection of inorganic oxidizers without increasing hardware complexity. The primary challenge for detection of inorganic oxidizers is the low vapor pressure of many of these materials. Low volatility analytes such as inorganic oxidizer salts (i.e., potassium chlorate) currently require thermal desorption or ionization source temperatures on the higher end of, or even exceeding, what is desirable for current detection devices, i.e. temperatures exceeding 350° C. Achieving such high temperatures is an engineering challenge specifically in smaller, field portable systems where size, weight and power must be minimized and long thermal cycling reduces sample throughput. Such high temperatures can also cause destruction of other more delicate analytes of interest (such as organic molecules) that may be coexistent in the analyzed sample. High temperatures can also increase the amount of background signal observed in a detection device, which decreases the quality of quantitative measurements.

The invention discloses reagents offering indirect detection of the analyte at lower temperatures. Take, for example, the inorganic oxidizer potassium perchlorate $KClO_4$, the detection of which is limited using conventional atmospheric pressure chemical ionization at temperatures less than about 350° C. Reagents are disclosed to chemically transform the anion of the oxidizer (e.g. perchlorate, $ClO_4^-$) into a much more volatile acid (e.g. perchloric acid, $HClO_4$). In this case, the perchloric acid has a much higher vapor pressure than its parent oxidizer salt, and is easily ionized to create $ClO_4^-$ which can be observed in negative ion detection mode. The acidic volatilizing reagent can also supply an anion (e.g. a phosphate) that can associate with cations of the oxidizing salt (e.g. $K^+$), providing charge balance and thermodynamic stability. The useful result of this concerted chemistry is increased availability of detectable anions (e.g. perchlorate) in the gas phase.

The reagents can be delivered by any reasonable method depending on the physical state of the reagent(s), as a solid, liquid or vapor. The introduction method can be via the solid state on or in a swipe or other substrate, liquid infused via nebulizer (inside or outside of an instrument), or by other practical means for introduction. In each of these embodiments, the objective is to broaden the range, type, and performance of volatilization reagents, which in turn allows for the API detection of a wider range of threat chemicals with greater signal intensities and better precision at lower temperatures. This advantage is important as the range of threats increases.

In one aspect, the volatilization reagents of this invention are specific for detection of inorganic oxidizers that will increase the amount of characteristic anions from the analyte entering the gas phase for subsequent detection. The presence of the volatilization reagent has the net effect of increasing the amount of signal detected from an analyte at a given temperature and allows for improved detection of these analytes at lower API source temperatures. Although volatilization reagents have been disclosed previously for other applications, there have been no previous disclosures of thermally or radiation transformable reagents for detection of inorganic oxidizers by API methods or the like.

In certain embodiments of the invention, the transformable or latent reagents can be thermally labile reagents, such as neutral inorganic salts. (The term "neutral" as used herein is intended to encompass reagents having a pH value greater than 6, typically between 6 and 8 at room temperature). Such reagents are stable at room temperatures but can undergo a transformation at higher temperatures in which the reagent decomposes into an acidic form to help volatilize or evaporate the target analyst. Acidification of the reagent preferably occurs at a temperature above 50 degrees C., or above 75 degrees C., and more preferably in some applications at temperatures above 100 or 150 degrees C. This property is particularly useful in conventional API ion mobility spectrometers, where thermal desorption of a potential analyte is preferably done at temperatures lower than the decomposition temperature of the swipe or other sample collection medium, e.g., less than about 250 degrees C.

By co-introduction of the latent reagent and the target analyte into the thermal desorption space of an instrument, the two can communicate with one another resulting in the protonation of the analyte's anion to form an acid molecule. The overall reaction is generally described as a salt metathesis reaction, where the acidic form of the reagent and the analyte salt effectively swap cations and anions with each other. The desired outcome of this reaction is a new acid, containing the anion of the originating analyte salt, where the acid is more volatile and hence easier to detect than the originating salt.

Thus, reaction schemes are disclosed in which a salt or other proton-donating reagent can react with an ionic analyte by exchanging the analyte's cation with a proton, and the corresponding association of the analyte's displaced cation with the reagent's anion, resulting in increased volatility of the analyte's protonated anion which thereby increases its detectability in an ion detection apparatus.

When neutral salts are used as thermally transformable or latent reagents, they can be, for example, phosphates, sulfates, nitrates, carbonates or borates. In some applications, inorganic salts such as phosphates are preferred. One particularly preferred, latent acid-generating, inorganic salt reagent is sodium phosphate monobasic monohydrate (SPMM). Other less preferred salts include sodium phosphate dibasic dihydrate ($Na_2HPO_4 \cdot 2H_2O$), sodium carbonate hydrate ($Na_2CO_3 \cdot H_2O$), sodium borate pentahydrate ($Na_2B_4O_7 \cdot 5H_2O$), sodium sulfite heptahydrate ($Na_2SO_3 \cdot 7H_2O$), magnesium sulfate heptahydrate ($MgSO_4 \cdot 7H_2O$) and sodium pyrophosphate hydrate ($Na_2H_2P_2O_7 \cdot H_2O$). The salts can comprise alkali metal salts (e.g., Na, Li, K, Rb or Cs salts) and/or alkaline earth metal salts (e.g., Mg, Ca, Sr, and Ba salts). The latent reagent can be in the solid or liquid phase. The acidity of the reagent, relative to that of the analyte, can also be tailored to provide reaction selectivity when compared to other analytes.

Radiation transformable reagents are also disclosed. For example, onium salts that decompose in response to actinic radiation to yield a constituent acid can also be used.

In practice, one ion (or more than one ion) can be formed for detection from interaction between the latent reagent and analyte(s). Analytes include, but are not limited to ionic components of explosives such as salts of chlorate, perchlorate, permanganate, dichromate, and osmium tetraoxide.

The methods of the present invention can be practiced where the reaction between the latent reagent and the analyte occurs on a dry, chemically treated collection swipe pre-impregnated with the latent reagent. In some embodiments, in addition to the reagent, an additional thermally labile hydrated salt can be incorporated into the pretreated swipe as an additional source of water upon heating. In such cases, the co-reagent can provide an additional source of water. In certain embodiments, an aqueous solution of the thermally labile hydrated salt preferably exhibits a pH between about 5 and 9. One example of a thermally labile hydrated salt co-reagent is sodium thiosulfate pentahydrate. In some embodiments, the swipe can contain both an inorganic salt as the latent reagent and sodium thiosulfate pentahydrate as a co-reagent source of water. (As noted above, sodium phosphate monobasic monohydrate is particularly preferred in some applications because, in addition to transforming into an acidic form when heated, its decomposition also results in the release of a water molecule.)

Other ways of providing water for the reaction can include reliance on ambient humidity or externally providing water (e.g., spraying the swab or providing a hydration source within the thermal desorption chamber.)

In other embodiments, the reaction between the latent reagent and the analyte can occur in the liquid phase after application of a liquid reagent-containing solution to a surface containing the analyte. For example, a liquid-phase latent reagent can be applied directly to a swipe containing the analyte. The liquid-phase latent reagent can also be applied within an ion detection apparatus prior to or during the heating of the analyte containing surface.

In another aspect of the invention, methods are disclosed for detection of an analyte molecule, X, potentially present in a sample, wherein the method includes, but is not limited to, treating the sample with a latent reagent (e.g., a thermally activated or photosensitive acid-forming reagent) to form a higher vapor pressure analog of the analyte if present in the sample, and subjecting the treated sample to mass spectrometry, whereby the presence of X in the sample can be deduced. The thus treated sample can then be subjected to mass spectrometry, e.g. ion mobility spectrometry or the like. The method can further include associating the latent reagent with a swipe prior to sample collection and then using the swipe to obtain a sample. It can also be preferable in some instances to employ hydrated latent acid-generating salts, in which there is at least one water molecule associated with at least some of the salt molecules.

In some instances, the methods and reagents of the present invention can be further enhanced by the addition of water-containing reagents or co-reagents. The presence of small quantities of water typically increases the effectiveness of the reactions disclosed herein. For example, sodium thiosulfate pentahydrate, $Na_2S_2O_3 \cdot 5H_2O$, can be introduced to the swipe material alongside one or more latent acidic volatilization reagents to supply additional water.

In a related aspect, a swipe for detection of an analyte molecule is disclosed, which includes a substrate configured to collect a sample for analysis, and a latent reagent (e.g., a heat or radiation-activated proton-donating reagent) that is associated with the substrate and is configured to react with the analyte, if present in the sample, so as to generate a higher vapor pressure (more volatile) analog of the analyte. The latent reagent can be associated with the substrate via a variety of mechanisms, such as physical entrainment, covalent and/or non-covalent bonds. The latent reagent can comprise any of the reagents disclosed above, or others apparent to those having ordinary skill in the art in view of the present teachings.

In a related aspect, a method for detection of an analyte molecule in a sample is disclosed, which comprises applying a latent evaporative reagent to a surface (e.g., a swipe or other sampling substrate) suspected of containing an analyte. Upon heating, the latent reagent is converted into an acidic reagent that can react with the analyte to generate the higher vapor pressure analyte analog (e.g., by proton donation). The latent reagent can be applied to the surface before or after contact with a suspect object. The reagent can be applied either in a solid state or a liquid state (e.g., via a reagent-containing solution). In some embodiments, the latent reagent is pre-applied to the swipe or is applied directly to a swipe surface suspected of containing the analyte following sample collection. In some embodiments, the latent reagent is applied within an ion detection apparatus (e.g., a mass spectrometer, such as an ion mobility spectrometer or a differential mobility spectrometer) prior to or during the heating of the analyte containing surface.

The acidity of the latent acid-generating reagent relative to that of the analyte can be tailored to provide reaction selectively when compared to other analytes. In some embodiments, the latent volatization reagent can be a solid-state acid. Generally speaking, methods for detection of an analyte, X, potentially present in a sample, are disclosed including the steps of treating the sample with an acidic evaporative reagent having a $pK_a$ of less than 6.0, or a $pK_a$ of less than 3.0, or a $pK_a$ of less than 2.5, or less than 2, or less than 0, or less than −2 to form a higher vapor pressure analog of the analyte if present in the sample, and subjecting the treated sample to mass spectrometry, whereby the presence of X in the sample can be deduced.

The methods disclosed herein can be practiced by subjecting the treated sample to mass spectrometry further comprises subjecting the treated sample to ion mobility spectrometry or differential mobility spectrometry. The methods can also be practiced by associating the latent reagent with a swipe prior to sample collection and then using the swipe to obtain a sample. The reagent can interact with the analyte if present in the sample either prior to desorption in a detection instrument or after it is released into a carrier gas along with any target analyte molecules captured by the swipe following desorption. The reagent can be a solid or liquid phase reagent applied to a substrate prior to collection of a sample for analysis.

Alternatively, the reaction between the acidic reagent can occur in the liquid phase after application of a latent reagent to a surface containing the analyte, for example by applying a reagent-containing solution to a swipe which has been used to collect a sample or by applying the latent reagent within an ion detection apparatus prior to or during the heating of the sample. The acidity of the reagent, relative to that of the analyte, can be tailored to provide reaction selectivity when compared to other analytes.

The methods disclosed herein can also be practiced by applying a co-reagent capable of releasing water or more specifically a thermally labile hydrate, such as for example, sodium bisulfate monohydrate or sodium phosphate monobasic monohydrate. Thus, methods for detection of an analyte molecule, X, potentially present in a sample, are disclosed including the steps of treating the sample with a latent acid-generating reagent and a co-reagent capable of releasing water to form a higher vapor pressure analog of the analyte if present in the sample, and subjecting the treated sample to mass spectrometry, whereby the presence of X in the sample can be deduced. The co-reagent can be a thermally labile hydrate, such as for example, sodium bisulfate monohydrate or sodium phosphate monobasic monohydrate, capable of releasing water upon heating. The step of subjecting the treated sample to mass spectrometry can further include subjecting the treated sample to ion mobility spectrometry or differential mobility spectrometry.

The acidic reagent and/or the co-reagent can be a solid or liquid phase reagent applied to a substrate, such as a swipe, prior to collection of a sample for analysis. The reagent can interact with the analyte if present in the sample either prior to desorption in a detection instrument or after it is released into a carrier gas along with any target analyte molecules captured by the swipe following desorption. In certain embodiments, the reaction between the acidic reagent and/or the co-reagent can occur in the liquid phase after application of a liquid-phase acidic reagent and/or the co-reagent to a surface containing the analyte, for example by applying a solution containing the reagent and/or the co-reagent to a swipe which has been used to collect a sample or by introducing the liquid-phase reagent and/or co-reagent into an ion detection apparatus prior to or during the heating of the sample.

In another aspect, swipes are disclosed for detection of an analyte molecule according to the various methods described herein. For example, the swipe can include a substrate configured to collect or receive a sample for analysis, and a latent acid-generating reagent associated with the substrate configured to react with an analyte, if present in the sample, so as to generate a higher vapor pressure analog of the analyte.

In yet another aspect, swipes are disclosed for detection of an analyte molecule according to the methods described herein. The swipe can include a substrate configured to collect or receive a sample for analysis, and an acidic reagent and a co-reagent capable of releasing water associated with the substrate and configured to react with an analyte, if present in the sample, so as to generate a higher vapor pressure analog of the analyte. The co-reagent can be a thermally labile hydrate, such as for example, sodium bisulfate monohydrate, capable of releasing water upon heating.

In certain embodiments, the acidic reagent and/or co-reagent can be applied to the swipe prior to, or after, collection of a sample. The co-reagent can be a thermally labile hydrate, such as for example, sodium bisulfate monohydrate, capable of releasing water upon heating. Alternatively, the latent reagent can be delivered to an ion detection apparatus, such as, a mass spectrometer, as a liquid infused via a nebulizer.

The invention is useful in a wide range of analyte detection apparatus, such as ion mobility spectrometers, differential mobility spectrometers, other mass spectrometers and any other apparatus where the sample is detected after it has vaporized.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings should not be considered to limit the scope of the invention.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

All publications, patents and patent applications cited herein, whether supra or infra, are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art. In case any further explanation might be needed, some terms have been further elucidated below.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. For instance, a concentration value of about 30% can mean a concentration between 27% and 33%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

In general, the pKa's of the latent evaporative reagents useful herein (upon activated into their acidic forms) are less than 6.0, or less than 3.0, or less than 2.5, or less than 2, or less than 0, or in some instances more preferably less than −2. Preferably, the latent acidic reagents according to the present invention convert strong oxidizers (chlorate, perchlorate) into their acidic forms (chloric acid, perchloric acid), while having both little to no discernable vapor pressure and chemical stability to >150° C., thus not off-gassing any unwanted vapors into the analysis instrument, and thereby allowing the analysis instrument to receive only the acidified oxidizers.

The term "swipe" is used herein in its general sense to mean a vehicle for collection of a sample. Typically in the context of ion mobility spectrometry used in security applications, the swipe is a substrate including at least one of paper, fabric, cloth, fibrous matte, gauze, cellulose, cotton, flax, linen, synthetic fibers and blends of such materials. However, other materials such as ceramic or semiconductor materials can also be used as "swipes" depending upon the analysis scheme.

The term "inorganic salt" as used herein is intended to cover any chemical compound of non-biological nature that is formed from the reaction of an acid with a base, with all or part of the hydrogen of the acid replaced by a metal or other cation, including, for example, phosphates, sulfates, nitrates, carbonates and borates. The salts can have various stoichiometries. For example, the term "phosphates" should be read to encompass monophophates, biphosphates, metaphosphates, pyrophosphates, dimers and higher order moieties.

Mass spectrometry is an analytical process for identifying a compound or compounds in a sample by assessing the molecular weight, chemical composition and structural information based on the mass-to-charge ratio of charged particles. Mass spectrometry is widely considered to have the best specificity of any technique applicable to a broad class of explosive compounds. In general, a sample undergoes ionization to form charged particles as ions; these charged particles are then passed through electric and/or magnetic fields to separate them according to their mass-to-charge ratio. The terms "mass spectrometry" and "spectrometry" are used herein to encompass techniques that produce a spectrum or spectra of the masses of molecules present in a sample. Mass spectrometry includes, but is not limited to, ion mobility spectrometry (IMS), differential mobility spectrometry (DMS), field asymmetric ion mobility spectrometry (FAIMS), and mass spectrometry (MS), all of which rely upon ionization of the analyte or a complex that includes the analyte. One analysis performed in spectrometry is typically referred to as "mass/charge" analysis, a method of characterizing the ions detected by a spectrometer in terms of their mass-to-charge ratio. The abbreviation m/z is used to denote the quantity formed by dividing the mass number of an ion by its charge number. It has long been called the mass-to-charge ratio although m is not the ionic mass nor is z a multiple or the elementary (electronic) charge, e. Thus, for example, for the ion $C_7H_7^{2+}$, m/z equals 45.5. In some instruments, e.g., atmospheric pressure instruments, a calculation of mass-to-charge is not necessary and the identification of species of interest can be accomplished by simply measuring ion mobility, e.g., the ions transit time through the instrument.

The ionization process can be performed by a wide variety of techniques, depending on the phase (solid, liquid, gas) of the sample and the efficiency of the target analyte(s) in question. Some examples of ion sources can include electron ionization, glow discharge ionization, resonant ionization, field desorption, fast atom bombardment, thermospray, desorption/ionization on silicon, atmospheric pressure chemical ionization, spark ionization, inductively coupled plasma ionization, secondary ionization by sputtering ion beams off the target's surface, and thermal ionization.

Ambient-pressure ionization, collision-induced ionization, and atmospheric-pressure chemical ionization refer to a characterization techniques in which picogram to microgram quantities of an analyte can be analyzed. The process generally refers to a chemical sample that is introduced into an ionization region as either a solid, liquid, or gas. In the ionization region, the analyte is in contact with other gases and ions that are part of the ionization region. Additional ions are produced through the collision of the analyte molecules with ions within the ionization reagent that are present in the ion source, electro-magnetic device. Inside the ion source, the ionization reagent is present in large excess compared to the analyte. Electrons and/or ions entering the source will preferentially ionize the ionization reagent. Collisions with other ionization reagent molecules will induce further ionization, creating positive and/or negative ions of the analyte. The ions are drawn into the spectrometer by either a carrier gas or focused into a beam by an electromagnet, then separated into individual beams based on the mass/charge ratio of the ions. The ion beams are separated in a mass spectrometer and collected either sequentially in a single detector or simultaneously in a set of multiple detectors to yield isotopic ratios. Highly accurate results require that sample cross-contamination be minimized.

The traditional methods for explosives detection usually involve wiping the ambient surface with a special material swipe followed by thermal desorption/gas phase ionization of the explosive compounds in the presence of an ionization reagent. The performance of a detection approach such as this depends, in part, on the efficiency with which the explosive compound is transferred from the swipe into the ionization region of the analysis instrument during the desorption step. It is therefore desirable to maximize this efficiency for explosive compounds that have low vapor pressures.

The terms "desorption," "desorb" and "desorbing" as used herein refer to technology of increasing the volatility of molecules, for example target analytes, such that they can be removed (separated) from the solid. Thermal desorption is not incineration, but uses heat and a flow of inert gas to extract volatile and semi-volatile molecules retained in a sample matrix or on a sorbent bed. The volatilized compounds are then either collected or thermally destroyed.

In certain embodiments, the latent reagents of the present invention are low volatility compounds. The terms "low volatility" and "low vapor pressure" as used herein are intended to describe compositions that do not readily evaporate or sublimate at room temperature (e.g., at about 25° C.). Typically such low volatility compositions are solids or viscous liquids and have a vapor pressure at room temperature of less than 1 Torr, or more typically less that $10^{-1}$ Torr. In some preferred embodiments, the low volatility reagents of the present invention can have a vapor pressure at room temperature of or less that $10^{-2}$ Torr or, more preferably, less that $10^{-3}$ Torr.

Figure 1:
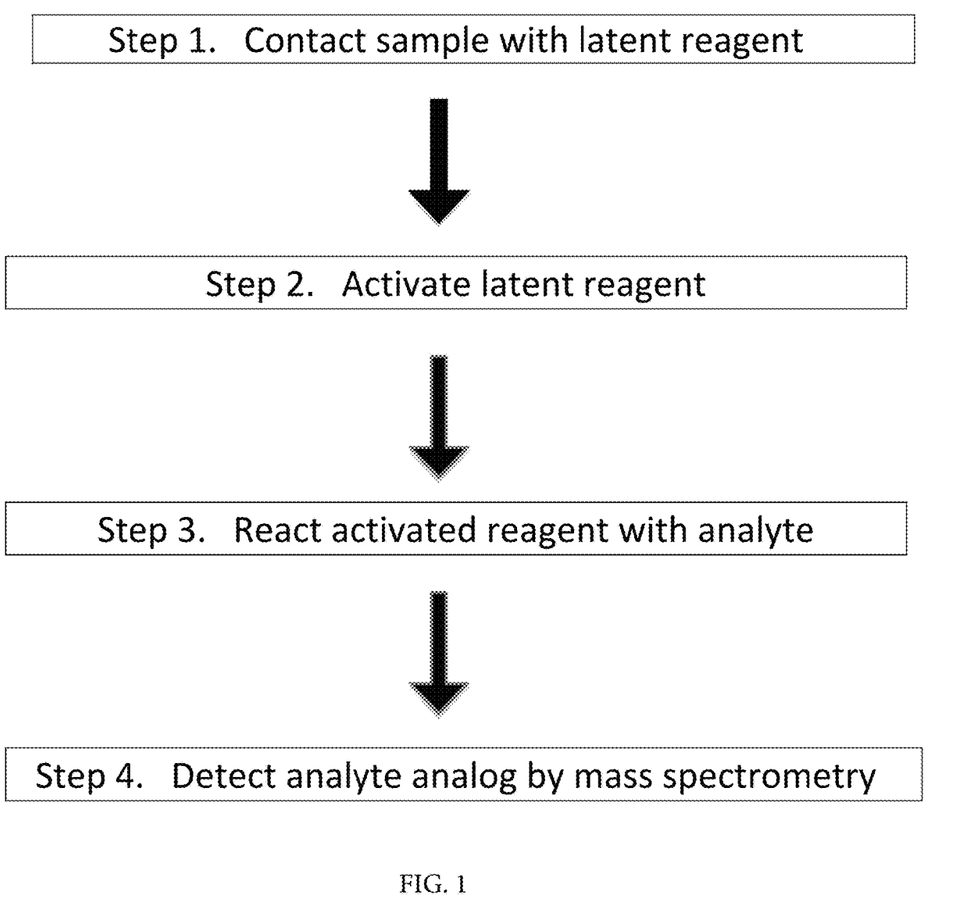
FIG. 1 is a flow diagram depicting various steps in a method according to an embodiment of the present invention for detection of an analyte molecule of interest in a sample.

With reference to flow chart of FIG. 1, a method is disclosed for detection of an analyte molecule potentially present in a sample, e.g., an inorganic oxidizer such as a chlorate or perchlorate. The method includes an initial step of contacting the sample with latent acid-generating reagent (step 1). The latent reagent is then activated (step 2). If the analyte is present on the swipe, it will react with acidified reagent (step 3) whereby a more volatile analog will be generated that can be ionized and subjected to mass spectroscopy to detect the analyte (step 4).

This invention also encompasses a material that is used for collecting chemical traces off surfaces (a "swab" or "swipe") for the purpose of presenting them to a detection instrument. The swab can include a latent vaporization reagent that can be turned on during or just prior to the thermal desorption of analytes from the swab material. In its inactivated form, the latent reagent maintains the swab in a near pH neutral state for the safe swabbing of surfaces (hands, luggage, etc.).

When the swab is then presented to the thermal desorber, the latent reagent, when exposed to a triggered energy source (either heat or ultraviolet light), undergoes a chemical transformation to become a more acidic reagent, rendering the swab pH acidic. The acidic reagent now created on the swab acts as a vaporization reagent to induce proton-cation exchange with inorganic salt analytes (e.g., chlorates, perchlorates, nitrates) to produce their corresponding acids of higher vapor pressure (e.g., chloric acid, perchloric acid, nitric acid) thereby rendering them more easily detected in the detection apparatus, without degradation of the detection of conventional explosive materials (TNT, RDX, PETN, etc.).

Thus, the presence of the latent vaporization reagent allows a single swab to collect and thermally release a wider range of analytes thereby expanding the useful range of detectable compounds by the detection apparatus. A further benefit to the swab embodiment may be obtained when choosing a latent vaporization reagent that releases water upon heating or ultraviolet light exposure, either by release of attached (molecular) water(s) of hydration or by consequence of the energy-induced chemical rearrangement of the latent vaporization reagent itself. Small quantities of water have been shown to enhance proton transfer from acidic reagents to analyte salts. An important advantage conferred by release of water by a latent vaporization reagent is the ability to detect trace quantities of inorganic salt analytes in dry (e.g., low humidity) operational environments.

The invention provides an improvement whereby the acidic functionality can be "turned on", thus allowing the swab to maintain a neutral pH during the swabbing process. This "turn on" process is mediated by an energetic conversion (heat or UV radiation) of one pH neutral reagent to a related reaction product which is acidic. The invention leverages the idea that acidic swabs are useful for detection of inorganic salt explosives, but that other analytes might prefer non-acidified swabs. One solution is to have two sets of swabs, one acidified and one not acidified. However, this solution requires two sets of swabs be purchased by the end user. In another aspect of the invention, a single swab type can be employed where the acidic functionality is latent and only activated when needed. This can be accomplished by an acid-generating molecule, where the acid is generated by heat or UV radiation at the time of use.

Figure 2:
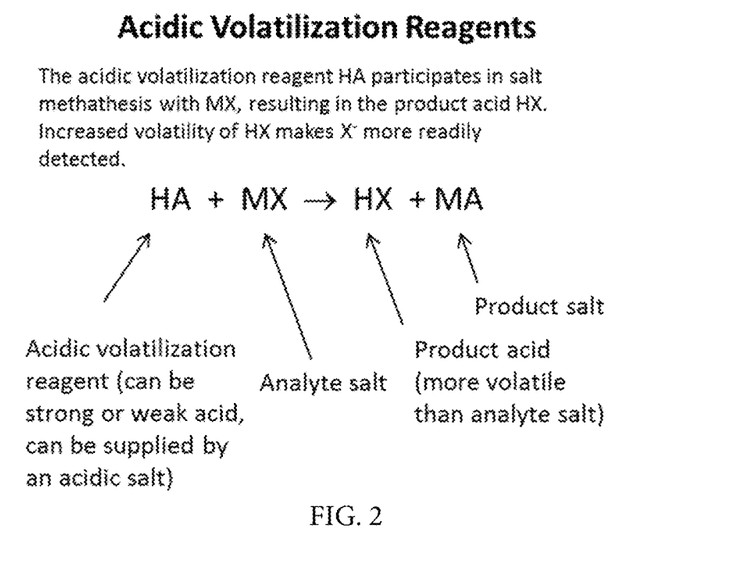
FIG. 2 illustrates an acidic volatilization reagent scheme according to the invention for detection of an oxidizer analyte. The acidic volatilization reagent exchanges its cation ($H^+$) and anion ($A^-$) with the oxidizer analyte salt to create an acid with the same anion as the analyte salt. The volatility of this acid increases the availability of the anion $A^-$ for detection in negative ionization mode.

FIG. 2 provides a reagent scheme (a salt metathesis) reaction for detection of an oxidizer in accordance with the present teachings, where a latent reagent is converted into an acidic volatilization reagent that induces a salt metathesis reaction to increase the availability of an originating salt's anion for detection in a negative ionization mode. The increased vapor pressure of the newly formed acid results in significantly increased detection sensitivity and the ability to perform the detection at lower temperatures.

In some embodiments, solid latent reagents (e.g. inorganic salts) can be a preferred method of providing an acidic reagent. These solids may be applied to existing swipes or introduced during manufacturing of chemically treated swipes. For example, hydrated forms of sodium phosphate easily decompose at low temperatures, liberating a weak acid, which is effective at participating in salt metathesis reactions. The presence of water typically increases the effectiveness of such reactions, and that too can be thermally released from a solid salt. Sodium phosphates can exist as monohydrates and can essentially supply their own water. One preferred latent reagent is sodium phosphate monobasic monohydrate (SPMM). Other hydrates exist, and when choosing one, three characteristics should be considered. First, the salt of the hydrate should not interfere with the desired salt methathesis reaction. More specifically, it should not compete with the analyte for protons. Secondly, the hydrate should decompose and release its hydrated water molecules at temperatures easily attainable in a thermal desorber (i.e., <200° C. or more preferably <150° C.). Lastly, the hydrate should contain as many associated water molecules as desired for the sake of efficiency.

Figure 3:
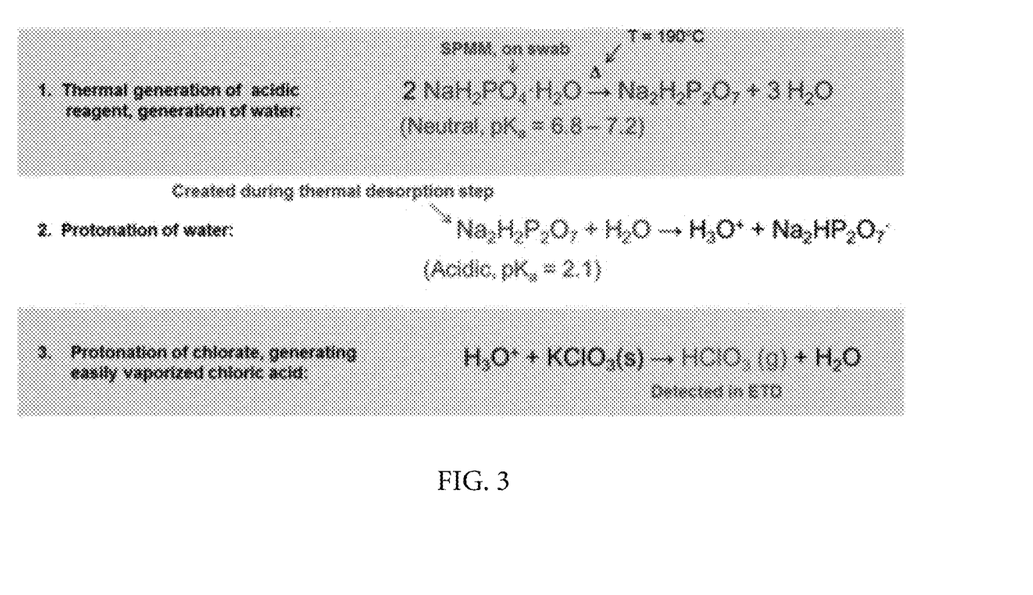
FIG. 3 is an illustration of a reaction mechanism for detecting potassium chlorate with one reagent according to the invention, sodium phosphate monobasic monohydrate (SPMM), FIG. 4 schematically depicts a swipe according to an embodiment of the present invention.

FIG. 3 illustrates a reaction mechanism by which SPMM chemically transforms upon heating to become a more acidic material (sodium pyrophosphate, $Na_2H_2P_2O_7$) while releasing water molecules beneficial to the detection mechanism is shown in FIG. 2.

The term "hydrate" as used herein is intended to encompass compositions in which there are one or more water molecules associated with at least some of the reagent or co-reagent molecules.

A series of acidic (or other) reagents may be utilized by introduction simultaneously or at discrete times and temperatures to induce selective reactions with expected oxidizers (e.g. reagent A for perchlorate, reagent B for chlorate, reagent C for hydrogen peroxide, reagent D for TATP, reagent E for HMTD). This invention will allow introduction of multiple reagents, if required for more selective detection.

An idealized latent reagent would convert the anions of inorganic oxidizer salts into their high vapor pressure acidic analogs and make no other contribution to the detectable ensemble of molecules in the gas phase. This could be accomplished by using an acid in which the counter anion (negatively charged component that remains after donating a proton) has a sufficiently low vapor pressure at the thermal desorption temperature. Another strategy involves tethering the counter anion to the substrate of the swipe used for sample gathering.

Figure 4:
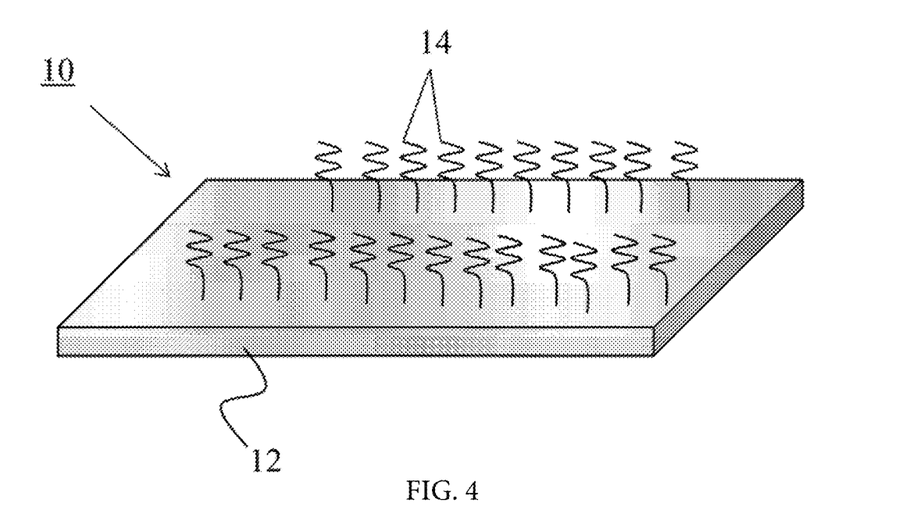

In some embodiments, swipes for use in detection of analytes of interest, such as, chlorates and perchlorates, are disclosed, which are impregnated with one or more latent evaporative reagents according to the present teachings. By way of example, FIG. 4 schematically depicts a swipe 10 (also referred to as swab, smear, or wipe) according to one embodiment, which includes a substrate 12. The substrate 12 can be formed of a variety of different materials, such as paper, fabric, cloth, fibers, glass, or synthetic material. By of example, in some embodiments, the substrate is fabricated of polyester, muslin, or cotton. The substrate can be preferably formed of a material that can be resistant to chemical degradation during testing in the approximate pH range of 0.1 through 14 to avoid reacting or decomposing. Further information regarding suitable substrates can be found in published U.S. patent application having publication no. 2014/0030816 entitled "Reagent Impregnated Swipe For Chemical Detection," which is herein incorporated by reference in its entirety.

One or more latent reagents, according to the present teachings, is deposited on, embedded in, or otherwise associated with, the substrate 10. The reagents 14 can be associated with the substrate via a variety of different physical and/or chemical mechanisms, such as physical entrainment, non-covalent and/or covalent bonds. In some embodiments, one or more latent regents can be associated with the substrate by tethering to the substrate, e.g. via covalent bonds. In some such embodiments, one or more linkers may be employed to tether the latent reagent to the substrate.

In some embodiments, the swipe 10 of FIG. 4 can be heat resistant, absorbent and/or chemically resistant at elevated temperatures and can have hydrophilic properties for wetting when using fluid reagents. While in some embodiments the swipe has a sheet-like structure, in other embodiments it can have a three-dimensional structure.

Commercial applications include use in all industries involved in chemical detection including but not limited to explosives detection, chemical warfare detection, homeland security, and toxic industrial chemical and pollution monitoring.

EXAMPLES

This invention has been reduced to practice for detection of potassium perchlorate, sodium perchlorate, potassium chlorate, potassium nitrate, sodium nitrate and sodium chlorate via API mass spectrometry. As described earlier, in negative-ion-mode atmospheric pressure chemical ionization, the vaporization (and hence ionization) efficiency of 'bare' oxidizer salts is extremely limited. The examples provided below are only for illustrative purposes, and are not intended to necessarily illustrate the optimal ways of practicing the invention and/or optimal results that may be obtained.

Example 1

Detection of a trace quantity of potassium chlorate with a swab treated with a latent vaporization reagent has been demonstrated on a commercial ETD system commonly found at airports. In these measurements, a commercially available swab material was treated with about 2-4 mg of sodium phosphate monobasic monohydrate (hereafter referred to as SPMM), a pH neutral salt typically used as a food additive. In this case, SPMM is being used as an example of a latent vaporization reagent. The treatment process involved first grinding and powdering the SPMM in a mortar and pestle, sprinkling the resulting powder on the surface of a commercial ETD swab, and further grinding that material (with the pestle alone) into the weave of the swab. The treated ETD swab was then shaken/tapped in order to allow excess SPMM powder to fall away. The treated swab was then used with the ETD system as any other ETD swab would be.

Table 1 shows the performance of SPMM treated swabs for detection of a trace quantity of potassium chlorate at two different thermal desorption temperatures (columns 2 and 3). This data shows that by adjusting the thermal desorption temperature, the detection enhancement capability of the SPMM treated swab can be 'turned on' as desired:

TABLE 1

| | Swabbed Surface Conditions | | |
|---|---|---|---|
| | Swab treated with SPMM, Desorption T = 205° C. | Swab trerated with SPMM, Desorption T = 100° C. | Swab treated with hydrated Naflon, Desorption T = 100° C. |
| Blank Teflon | No alarm | No alarm | No alarm |
| Trace KClO$_3$ on Teflon | Chlorate alarm | No alarm | Chlorate alarm |
| Trace KClO$_3$ on Teflon | Chlorate alarm | No alarm | Chlorate alarm |
| Trace KClO$_3$ on Teflon | Chlorate alarm | No alarm | Chlorate alarm |
| Trace KClO$_3$ on Teflon | Chlorate alarm | No alarm | Chlorate alarm |
| Trace KClO$_3$ on Teflon | Chlorate alarm | No alarm | Chlorate alarm |
| Blank Teflon | No alarm | No alarm | No alarm |

Table 1 illustrates the instrument alarms for swabs treated with SPMM latent vaporization reagent as a function of swabbed surface conditions and temperature. At T=205° C., the SPMM is activated and the correct alarm status is realized (in green). At T=105° C., the SPMM remains pH neutral and alarms are not reported (red). The third column demonstrates that detection of chlorate is possible at T=105° C., if the swab is suitably acidic (using a polymeric acid reagent, Nafion®, a sulfonated tetrafluoroethylene based fluoropolymer-copolymer, which is described further in parent application, now U.S. Pat. No. 10,345,281 entitled "Reagents For Enhanced Detection of Low Volatility Analytes.

As is evident in the second column of Table 1, SPMM, despite its neutral acidity, enables the trace detection of chlorate when it is exposed to the hot (205° C.) environment of the thermal desorption front end of the ETD system. This is because the SPMM transforms into a more acidic material during the thermal desorption process. In the case of the other 'no alarm' entries in Table 1, the SPMM was not heated to a sufficient temperature (because the thermal desorber temperature was purposely dialed back) to allow it to transform into a sufficiently acidic material to enable detection of the trace quantity of chlorate salt. Further supporting measurements (column 4) were conducted with normally acidic swabs (containing Nafion®, which is always acidic) at a thermal desorption temperature of 100° C., and it was demonstrated that the detection of trace chlorate works perfectly well at 100° C., if the swab is suitably acidified.

Figure 5:
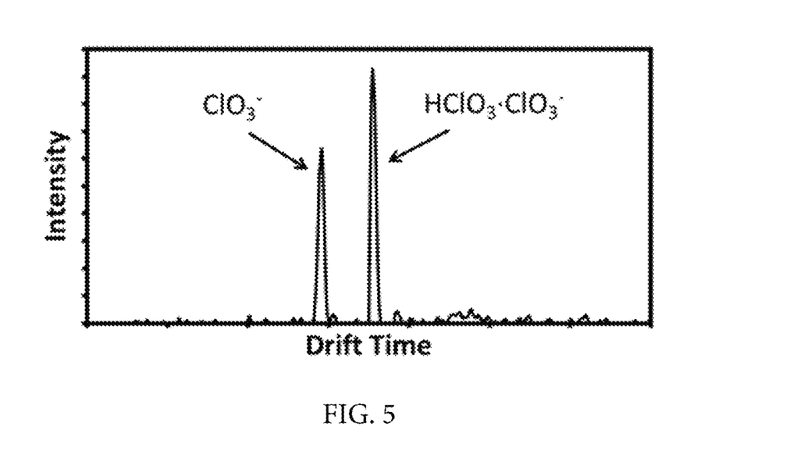
FIG. 5 is a background subtracted plasmagram of trace potassium chlorate sample measured with a SPMM treated swab presented to a laboratory IMS instrument.

FIG. 5 shows a background-subtracted plasmagram from a laboratory IMS system detecting trace potassium chlorate with an SPMM treated swab. Note that the peaks corresponding to the presence of chlorate ($ClO_3^-$) and the chloric acid/chlorate dimer ($HClO_3 \cdot ClO_3^-$) are the only prominent peaks in the subtracted plasmagram.

In the presence of a sufficiently acidic reagent, the potassium chlorate salt exchanges its potassium with a proton to become chloric acid ($HClO_3$), which can subsequently shed its proton to become detected chlorate anions ($ClO_3^-$) or react with another chloric acid molecule to produce a detected chloric acid dimer ($HClO_3 \cdot ClO_3^-$).

Figure 6:
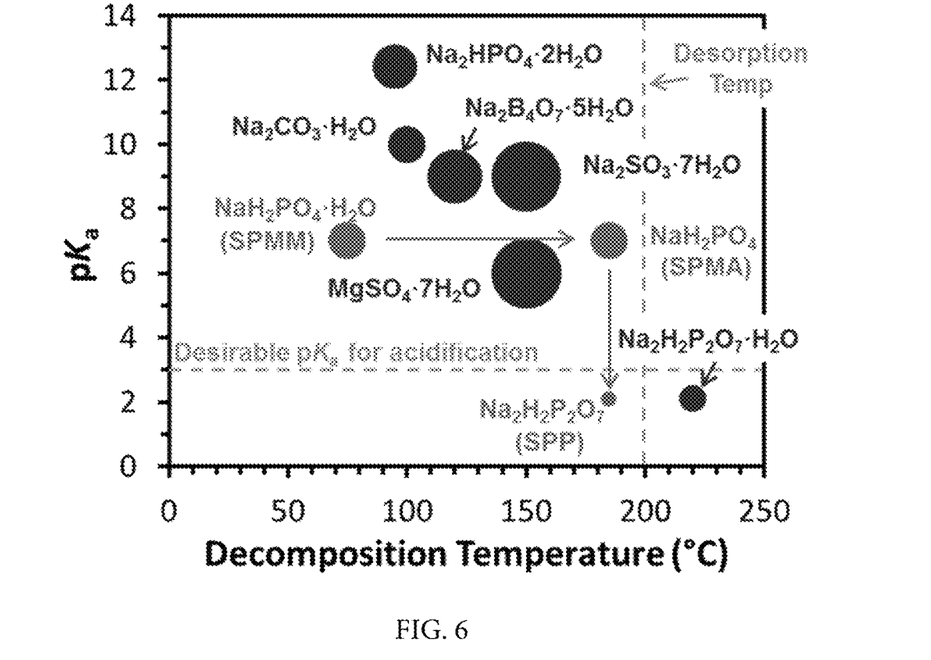
FIG. 6 shows how sodium phosphate monobasic monohydrate (SPMM) undergoes both release of a water molecule and conversion to a more acidic molecule, both of which benefit the process described in this invention, upon heating to temperatures between 150 and 220 degrees C.

FIG. 6 provides a chart of inorganic salts that release water as a function of decomposition temperature vs $pK_a$ of the salt. The size of each circle is proportional to the relative weight percent of water in the hydrated salt. This chart can help identify preferred compounds. The two requirements for a preferred compound is that it thermally decomposes to release water at temperatures below 200° C. (e.g., to the left of the vertical dashed line labeled "Desorption Temperature"), and that it has a $pK_a$ below 3 (e.g., below the horizontal dashed line labeled "Desirable $pK_a$ for acidification". From this chart, we see that many salts decompose within the desired temperature range, but they have too high a $pK_a$. These non-preferred compounds are colored in blue. However, the SPMM (colored in green) undergoes two reactions which, when combined, release water and produce an acid with a $pK_a<3$. For this reason SPMM is a particularly preferred latent reagent according to the invention. Other salts showing similar behavior, but not shown on the chart, could also potentially work. For example, one would expect similar salts of lithium (Li), potassium (K), rubidium (Rb), or cesium (Cs) to show similar trends and provide similar performance features to their sodium containing analogs. Likewise, for compounds possessing two alkali bases, such as sodium pyrophosphate hydrate ($Na_2H_2P_2O_7 \cdot H_2O$), there are analogs that contain divalent alkaline earth compounds (i.e., Mg, Ca, Sr, Ba) that may also similarly function.

Figure 7:
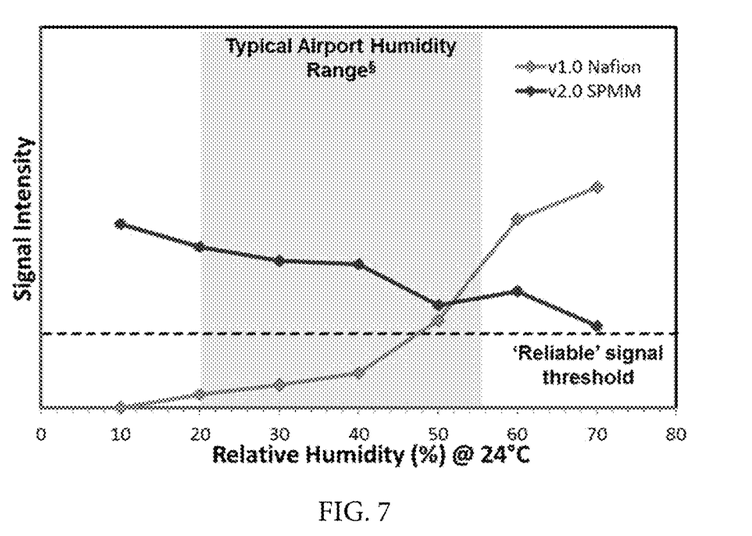
FIG. 7 shows how a acidification reagent that releases latent water (SPMM) performs well at low humidity when compared to an acidification reagent that does not release latent water (Nafion®). (Note: Nafion® is a sulfonated tetrafluoroethylene based fluoropolymer-copolymer, which is described further in co-pending, parent application, U.S. patent application Ser. No. 14/679,891 entitled "Reagents For Enhanced Detection of Low Volatility Analytes" filed Apr. 6, 2015)

FIG. 7 is a chart showing humidity dependence v1.0 Nafion® versus v2.0 SPMM reagents on the swab. In this chart, the benefits of the water-releasing properties of the SPMM are apparent. Note that the Nafion® acidification reagent may not adequately vaporize potassium chlorate at humidity values <50% (blue curve), whereas the SPMM can despite its much higher $pK_a$ (i.e., weaker acid) value.

Figure 8:
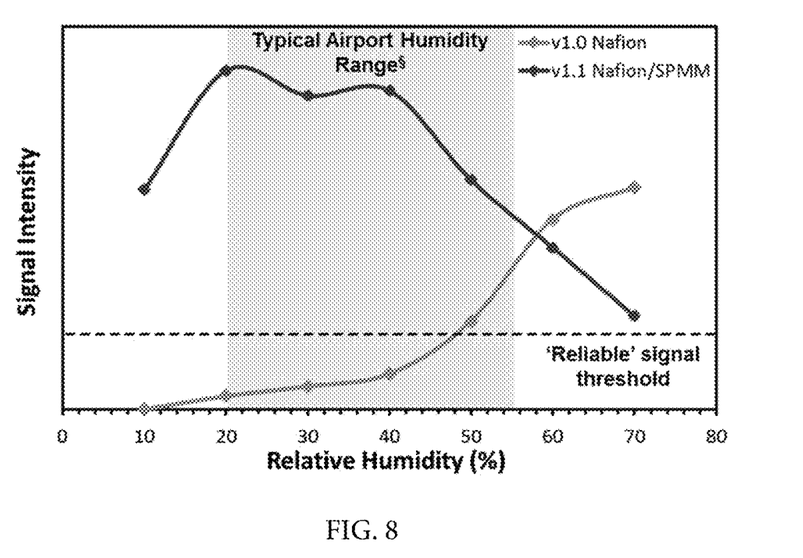
FIG. 8 shows that by combination of a strong acidification reagent (Nafion®) with a weak acidification reagent that releases latent water (SPMM), the detection is greatly enhanced over a wide range of ambient humidity levels.

FIG. 8 is a chart showing humidity dependence of v1.1 Nafion® swab with SPMM as a co-reagent compared to v1.0 Nafion® swab alone. Here we see that the hydration properties of the SPMM allow it to act as an effective co-reagent with the much more strongly acidic Nafion®. This is evident from the fact that the co-reagent ability to vaporize potassium chlorate (red curve) yields better results than either of the two reagents used alone (the two curves in the previous figure).

Example 2

Ultraviolet activated swab chemistry is an alternative approach, whereby the energy required to change the latent vaporization reagent into a more acidic material is provided by UV light (or other forms of high energy radiation) rather than by a source of thermal energy.

Figure 9:
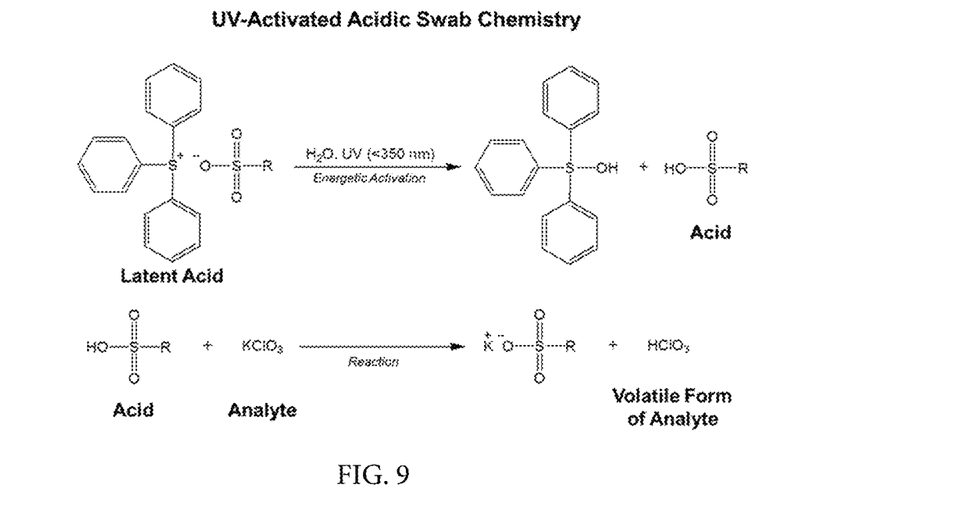
FIG. 9 illustrates another reaction mechanism for detection of potassium chlorate with a UV-activated acidic swab chemistry, where the reagent is a small molecule.

FIG. 9 shows a scheme whereby UV energizes a latent acid (in this case a sulfonium cation ion coordinated with a sulfonate anion) and causes it to release a sulfonic acid molecule that actively participates in enhancing detection of an analyte salt. This type of swab chemistry can be used in an ETD instrument equipped with integral UV lights, or with a portable UV light source located external to the ETD instrument.

Figure 10:
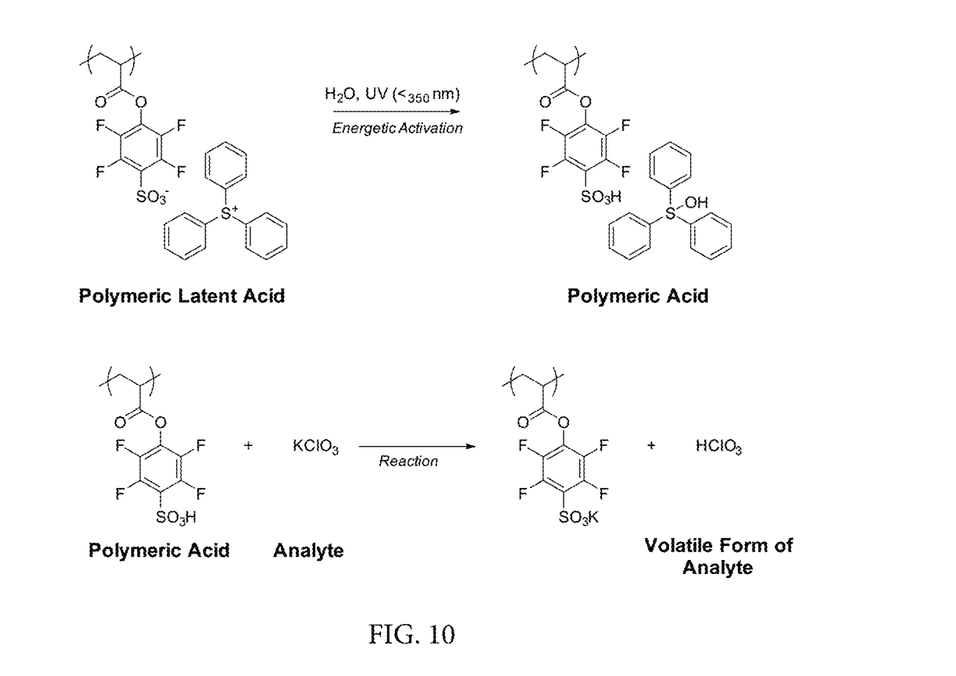
FIG. 10 illustrates another reaction mechanism for detection of potassium chlorate with a UV-activated acidic swab chemistry, where the reagent is a polymer.

FIG. 10 provides a further example of a polymeric onium salt useful in the present invention.

One skilled in the art will appreciate further features and advantages of the invention based on the above-described embodiments. Accordingly, the invention is not to be limited by what has been particularly shown and described, except as indicated by the appended claims. All patents, publications and references cited herein are expressly incorporated herein by reference in their entirety.

The invention claimed is:

1. A method for detection of an analyte molecule, X, potentially present in a sample, the method comprising:
   contacting the sample with a latent acid-generating reagent;
   chemically activating the latent reagent to provide an activated acidic reagent;
   reacting the activated reagent with the analyte to form a higher vapor pressure analog of the analyte if present in the sample, and
   subjecting the sample to mass spectrometry, whereby the presence of X in the sample can be deduced by detection of the higher vapor pressure analog of the analyte;
   wherein the latent reagent comprises an inorganic salt.

2. The method of claim 1, wherein the latent acid-generating reagent has a $pK_a$ of greater than 6 prior to activation and a $pK_a$ of less than 6 following activation.

3. The method of claim 2, wherein the latent acid-generating reagent has a $pK_a$ of less than 3 following activation.

4. The method of claim 2, wherein the latent acid-generating reagent has a $pK_a$ of less than 2.5 following activation.

5. The method of claim 1, wherein the latent reagent comprises an inorganic salt selected from the group of phosphates, sulfates, nitrates, carbonates and borates.

6. The method of claim 1, wherein the step of chemically activating the reagent further comprises subjecting the reagent to radiation.

7. The method of claim 1, wherein the step of chemically activating the reagent further comprises subjecting the reagent to UV radiation.

8. The method of claim 1, wherein the step of subjecting the sample to mass spectrometry further comprises subjecting the sample to ion mobility spectrometry.

9. A method for detection of an analyte molecule, X, potentially present in a sample, the method comprising:
   contacting the sample with a latent acid-generating reagent;
   chemically activating the latent reagent to provide an activated acidic reagent;
   reacting the activated reagent with the analyte to form a higher vapor pressure analog of the analyte if present in the sample, and
   subjecting the sample to mass spectrometry, whereby the presence of X in the sample can be deduced by detection of the higher vapor pressure analog of the analyte;
   wherein the reagent comprises an inorganic salt selected from the group of alkali metal salts and alkaline earth metal salts.

10. The method of claim 9, wherein the inorganic salt further comprises a hydrated inorganic salt.

11. The method of claim 9, wherein the inorganic salt further comprises a hydrated phosphate.

12. The method of claim 11, wherein the inorganic salt further comprises a hydrated sodium phosphate.

13. The method of claim 11, wherein the inorganic salt further comprises sodium phosphate monobasic monohydrate (SPMM).

14. A method for detection of an analyte molecule, X, potentially present in a sample, the method comprising:
   contacting the sample with a latent acid-generating reagent;
   chemically activating the latent reagent to provide an activated acidic reagent;
   reacting the activated reagent with the analyte to form a higher vapor pressure analog of the analyte if present in the sample; and
   subjecting the sample to mass spectrometry, whereby the presence of X in the sample can be deduced by detection of the higher vapor pressure analog of the analyte;
   wherein the step of chemically activating the reagent further comprises heating the reagent.

15. A method for detection of an analyte molecule, X, potentially present in a sample, the method comprising:
   contacting the sample with a latent acid-generating reagent;
   chemically activating the latent reagent to provide an activated acidic reagent;
   reacting the activated reagent with the analyte to form a higher vapor pressure analog of the analyte if present in the sample, and
   subjecting the sample to mass spectrometry, whereby the presence of X in the sample can be deduced by detection of the higher vapor pressure analog of the analyte;
   wherein the reagent comprises an onium salt.

16. A method for detection of an analyte molecule, X, potentially present in a sample, the method comprising:
   contacting the sample with a latent acid-generating reagent;
   chemically activating the latent reagent to provide an activated acidic reagent;
   reacting the activated reagent with the analyte to form a higher vapor pressure analog of the analyte if present in the sample; and
   subjecting the sample to mass spectrometry, whereby the presence of X in the sample can be deduced by detection of the higher vapor pressure analog of the analyte;
   wherein the method further comprises associating the latent acid-generating reagent with a swipe prior to sample collection and then using the swipe to obtain a sample.

17. The method of claim 16, wherein the reagent interacts with the analyte if present in the sample either prior to desorption in a detection instrument or after it is released into a carrier gas along with any target analyte molecules captured by the swipe following desorption.

18. The method of claim 1, A method for detection of an analyte molecule, X, potentially present in a sample, the method comprising:
   contacting the sample with a latent acid-generating reagent;
   chemically activating the latent reagent to provide an activated acidic reagent;
   reacting the activated reagent with the analyte to form a higher vapor pressure analog of the analyte if present in the sample; and
   subjecting the sample to mass spectrometry, whereby the presence of X in the sample can be deduced by detection of the higher vapor pressure analog of the analyte;
   wherein the method further comprises applying a co-reagent to the sample that releases water.

19. The method of claim 18 wherein the co-reagent is a thermally labile hydrate.

* * * * *